United States Patent
Ito et al.

(10) Patent No.: US 9,637,604 B2
(45) Date of Patent: May 2, 2017

(54) STERILIZED OXYGEN-ABSORBING RESIN COMPOSITION, STERILIZED OXYGEN-ABSORBING MULTILAYER CONTAINER AND METHOD FOR PRODUCING THE SAME

(71) Applicant: MITSUBISHI GAS CHEMICAL COMPANY, INC., Tokyo (JP)

(72) Inventors: Fumihiro Ito, Kanagawa (JP); Satoshi Okada, Kanagawa (JP); Shinpei Iwamoto, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/115,787

(22) PCT Filed: Feb. 6, 2015

(86) PCT No.: PCT/JP2015/053325
§ 371 (c)(1),
(2) Date: Aug. 1, 2016

(87) PCT Pub. No.: WO2015/119230
PCT Pub. Date: Aug. 13, 2015

(65) Prior Publication Data
US 2017/0009035 A1    Jan. 12, 2017

(30) Foreign Application Priority Data

Feb. 6, 2014  (JP) ................................. 2014-021347

(51) Int. Cl.

| | | |
|---|---|---|
| *C08J 7/12* | (2006.01) | |
| *B01J 20/26* | (2006.01) | |
| *B01J 20/22* | (2006.01) | |
| *B01J 20/30* | (2006.01) | |
| *C08G 63/189* | (2006.01) | |
| *C08K 3/24* | (2006.01) | |
| *B65B 55/08* | (2006.01) | |
| *B32B 27/08* | (2006.01) | |
| *B32B 27/36* | (2006.01) | |
| *B32B 27/20* | (2006.01) | |
| *B32B 27/16* | (2006.01) | |
| *B32B 27/32* | (2006.01) | |

(52) U.S. Cl.
CPC ............. *C08J 7/123* (2013.01); *B01J 20/223* (2013.01); *B01J 20/262* (2013.01); *B01J 20/3078* (2013.01); *B32B 27/08* (2013.01); *B32B 27/16* (2013.01); *B32B 27/20* (2013.01); *B32B 27/32* (2013.01); *B32B 27/36* (2013.01); *B65B 55/08* (2013.01); *C08G 63/189* (2013.01); *C08K 3/24* (2013.01); *B32B 2250/24* (2013.01); *B32B 2307/74* (2013.01); *B32B 2439/70* (2013.01); *B32B 2439/80* (2013.01); *C08G 2390/00* (2013.01); *C08J 2367/02* (2013.01); *C08K 2201/012* (2013.01)

(58) Field of Classification Search
CPC ...... C08J 7/123; C08J 2367/02; B01J 20/262; B01J 20/223; B01J 20/3078; C08G 63/189; C08G 2390/00; C08K 3/24; C08K 2201/012; B65B 55/08; B32B 27/08; B32B 27/36; B32B 27/20; B32B 27/16; B32B 27/32; B32B 2250/24; B32B 2307/74; B32B 2439/70; B32B 2439/80
See application file for complete search history.

(56) References Cited

U.S. PATENT DOCUMENTS

2014/0373485 A1    12/2014 Okada et al.

FOREIGN PATENT DOCUMENTS

| JP | 2-13460 | 1/1990 |
|---|---|---|
| JP | 2000-5283 | 1/2000 |
| WO | 2013/077436 | 5/2013 |
| WO | 2013/089268 | 6/2013 |
| WO | 2013/118882 | 8/2013 |

OTHER PUBLICATIONS

International Search Report issued in Japanese Patent Application No. PCT/JP2015/053325, dated Apr. 21, 2015.
International Preliminary Report on Patentability issued in PCT/JP2015/053325, dated Aug. 9, 2016.

*Primary Examiner* — Michael C Miggins
(74) *Attorney, Agent, or Firm* — Greenblum & Bernstein, P.L.C.

(57) ABSTRACT

The present invention provides a sterilized oxygen-absorbing resin composition obtained by performing at least: a sterilizing step of irradiating with radiation an oxygen-absorbing resin composition containing a transition metal catalyst and a thermoplastic resin (a) having a tetralin ring as a constituent unit; and a step of heating the oxygen-absorbing resin composition at a temperature equal to or higher than the glass transition temperature of the thermoplastic resin (a) and equal to or lower than 200° C., after the sterilizing step.

10 Claims, No Drawings

STERILIZED OXYGEN-ABSORBING RESIN COMPOSITION, STERILIZED OXYGEN-ABSORBING MULTILAYER CONTAINER AND METHOD FOR PRODUCING THE SAME

TECHNICAL FIELD

The present invention relates to an oxygen-absorbing resin composition, a sterilized oxygen-absorbing multilayer container and a method for producing the same.

BACKGROUND ART

Gamma sterilization using $Co^{60}$, which is a radioisotope of Co, as a radiation source has been common for many years as a radiation sterilization method of containers used for food, beverages, drugs, cosmetics, and the like. Other radiation sterilization methods include treatment by X-rays or electron beams. The radiation sterilization has been widely spreading as a sterilization treatment method because containers can be treated at a low temperature, in a short time, and at a relatively low cost.

On the other hand, for the purpose of preventing oxygen oxidation of various articles liable to change in quality or deteriorate in response to the influence of oxygen, which are typified by food, beverages, drugs, and cosmetics, to thereby store them for a long period of time, there has been used an oxygen absorber to remove oxygen in a package containing these articles.

Further, there have been developed oxygen-absorbing resin compositions each containing a transition metal catalyst and a polymer having a predetermined tetralin ring and multilayer containers using the same (refer to Patent Literatures 1 to 3).

CITATION LIST

Patent Literature

Patent Literature 1: International Publication No. WO 2013-077436
Patent Literature 2: International Publication No. WO 2013-089268
Patent Literature 3: International Publication No. WO 2013-118882

SUMMARY OF INVENTION

Technical Problem

However, a problem of the oxygen-absorbing resin composition and the multilayer container of Patent Literature 1 is that when they are sterilized by irradiation with radiation such as gamma rays, X-rays, and electron beams, the resin composition and the multilayer container will be colored and require a long time to fade. Further, depending on the degree of coloration, not only the appearance of the container deteriorates, but the identification of the liquid surface and color of the contents of the container becomes difficult, which is a problem with respect to the visibility.

The present invention has been made in view of the above circumstances, and an object of the present invention is to provide a sterilized oxygen-absorbing resin composition and a sterilized oxygen-absorbing multilayer container which are suppressed in coloration even after sterilized by irradiation with radiation such as gamma rays, X-rays, and electron beams.

Solution to Problem

As a result of investigation of oxygen-absorbing resin compositions and oxygen-absorbing multilayer containers, the present inventors have found that the above problems can be solved by performing heat treatment under a predetermined condition after the sterilization treatment with radiation such as gamma rays, X-rays, and electron beams, and have completed the present invention.

Specifically, the present invention provides the following <1> to <10>.
<1>
A sterilized oxygen-absorbing resin composition obtained by performing at least
a sterilizing step of irradiating with radiation an oxygen-absorbing resin composition comprising a transition metal catalyst and a thermoplastic resin (a) having a tetralin ring as a constituent unit; and
a step of heating the oxygen-absorbing resin composition at a temperature equal to or higher than a glass transition temperature of the thermoplastic resin (a) and equal to or lower than 200° C., after the sterilizing step.
<2>
The sterilized oxygen-absorbing resin composition according to <1>, wherein a time of the heating is 1 to 120 minutes.
<3>
The sterilized oxygen-absorbing resin composition according to <1> or <2>, wherein the thermoplastic resin (a) is a polyester compound comprising a constituent unit having at least one tetralin ring selected from the group consisting of the following general formulas (1) to (4):

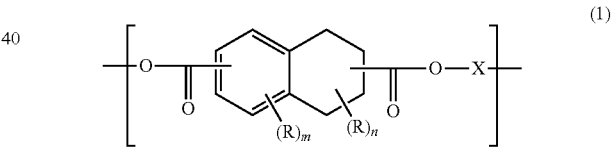

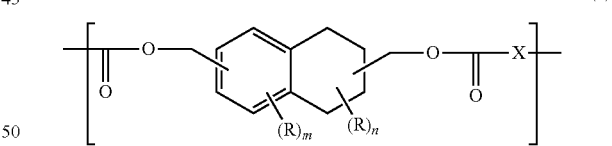

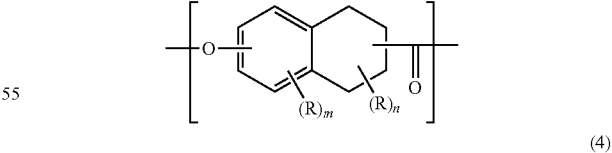

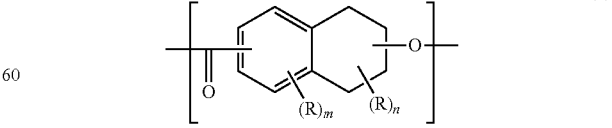

wherein R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, these of which may further have a substituent; m represents an integer of 0 to 3; n represents an integer of 0 to 7; at least one hydrogen atom is bonded to a benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

<4>
The sterilized oxygen-absorbing resin composition according to any one of <1> to <3>, wherein the transition metal catalyst comprises at least one transition metal selected from the group consisting of manganese, iron, cobalt, nickel, and copper.

<5>
The sterilized oxygen-absorbing resin composition according to any one of <1> to <4>, wherein the transition metal catalyst is contained in an amount of 0.001 to 10 parts by mass in terms of the amount of a transition metal based on 100 parts by mass of the thermoplastic resin (a).

<6>
The sterilized oxygen-absorbing resin composition according to any one of <1> to <5>, wherein the constituent unit represented by the general formula (1) is at least one selected from the group consisting of the following formulas (5) to (7).

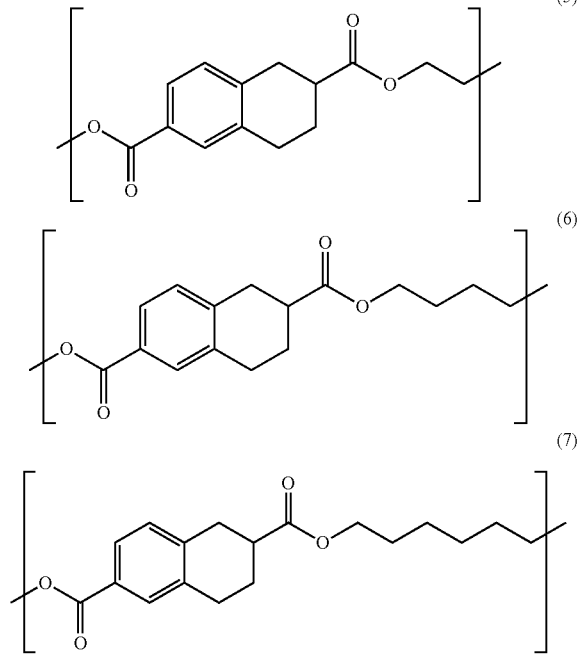

<7>
The sterilized oxygen-absorbing resin composition according to any one of <1> to <6>, wherein the radiation is at least one selected from the group consisting of gamma rays, X-rays, and electron beams.

<8>
A sterilized oxygen-absorbing multilayer container obtained by performing at least:
a sterilizing step of irradiating with radiation an oxygen-absorbing multilayer container comprising an oxygen-absorbing multilayer body, wherein the oxygen-absorbing multilayer body comprises at least an oxygen absorbing layer (layer A) comprising an oxygen-absorbing resin composition comprising a transition metal catalyst and a thermoplastic resin (a) having a tetralin ring as a constituent unit and a layer (layer B) comprising a thermoplastic resin (b) formed on the oxygen absorbing layer (layer A); and
a step of heating the oxygen-absorbing multilayer container at a temperature equal to or higher than the glass transition temperature of the thermoplastic resin (a) and equal to or lower than 200° C., after the sterilizing step.

<9>
The sterilized oxygen-absorbing multilayer container according to <8>, wherein:
the oxygen-absorbing multilayer container comprises an oxygen-absorbing multilayer body having three or more layers, the oxygen-absorbing multilayer body comprising at least
the oxygen absorbing layer (layer A),
a layer (layer B1) comprising a thermoplastic resin (b1) formed on one surface of the oxygen absorbing layer (layer A), and
a layer (layer B2) comprising a thermoplastic resin (b2) formed on another surface of the oxygen absorbing layer (layer A); and
the temperature of the heating step is equal to or higher than the glass transition temperature of the thermoplastic resin (a) and equal to or lower than either a glass transition temperature of the thermoplastic resin (b1) or a glass transition temperature of the thermoplastic resin (b2).

<10>
A method for producing a sterilized oxygen-absorbing multilayer container, comprising:
a sterilizing step of irradiating with radiation an oxygen-absorbing multilayer container comprising an oxygen-absorbing multilayer body, wherein the oxygen-absorbing multilayer body comprises at least an oxygen absorbing layer (layer A) comprising an oxygen-absorbing resin composition comprising a transition metal catalyst and a thermoplastic resin (a) having a tetralin ring as a constituent unit and a layer (layer B) comprising a thermoplastic resin (b) formed on the oxygen absorbing layer (layer A); and
a step of heating the oxygen-absorbing multilayer container at a temperature equal to or higher than a glass transition temperature of the thermoplastic resin (a) and equal to or lower than 200° C., after the sterilizing step.

Advantageous Effects of Invention

The present invention can provide a sterilized oxygen-absorbing resin composition and a sterilized oxygen-absorbing multilayer container which are suppressed in coloration even after being sterilized by radiation such as gamma rays, X-rays, and electron beams. Thereby, the resin composition and the multilayer container can be used even in the applications in which sterilization treatment with radiation is required. Therefore, they can be used in wide applications as a container, for example, for food, cooked food, beverages, drugs, and health food.

DESCRIPTION OF EMBODIMENTS

Hereinafter, the embodiment of the present invention (hereinafter simply referred to as "the present embodiment")

will be described in detail. The present embodiment to be described below is for illustration purposes to describe the present invention and not intended to limit the present invention to the following contents. The present invention can be carried out by suitably modifying the contents within the scope of the present invention.

The sterilized oxygen-absorbing resin composition of the present embodiment is a sterilized oxygen-absorbing resin composition obtained by performing at least a sterilizing step of irradiating with radiation an oxygen-absorbing resin composition comprising a transition metal catalyst and a thermoplastic resin (a) having a tetralin ring as a constituent unit; and, after the sterilizing step, a step of heating the oxygen-absorbing resin composition at a temperature equal to or higher than the glass transition temperature of the thermoplastic resin (a) and equal to or lower than 200° C. Generally, when such a composition is sterilized by radiation irradiation, the composition will be colored. However, the present inventors have unexpectedly found that the coloration of the composition by radiation irradiation can be faded in a short time by heating the composition in a temperature range equal to or higher than the glass transition temperature of the thermoplastic resin (a) and equal to or lower than 200° C. (however, the mechanism of the present embodiment is not limited to these). Hereinafter, each component will be described.

[Oxygen-Absorbing Resin Composition]

The oxygen-absorbing resin composition of the present embodiment is not limited at all as long as it contains a transition metal catalyst and a thermoplastic resin (a) having a tetralin ring as a constituent unit, but known materials can be used as the oxygen-absorbing resin composition. For example, polymers each having a tetralin ring such as those described in International Publication No. WO 2013-077436, International Publication No. WO 2013-089268, and International Publication No. WO 2013-118882 can also be used.

[Thermoplastic Resin (a)]

From the point of view of oxygen-absorbing performance, the thermoplastic resin (a) is preferably a polyester compound having a tetralin ring as a constituent unit, more preferably a polyester compound (a) comprising a constituent unit having at least one tetralin ring selected from the group consisting of the following general formulas (1) to (4). Note that, hereinafter, the polyester compound containing a constituent unit having a tetralin ring may be referred to as a tetralin ring-containing polyester compound.

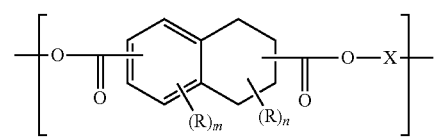 (1)

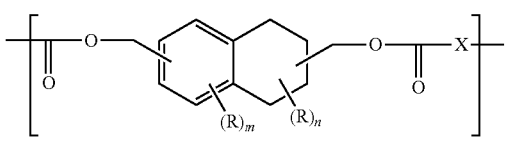 (2)

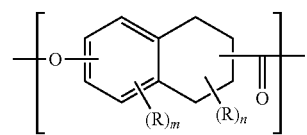 (3)

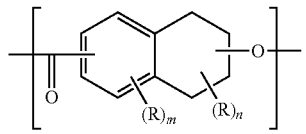 (4)

In the formulas, R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, these of which may further have a substituent; m represents an integer of 0 to 3; n represents an integer of 0 to 7; at least one hydrogen atom is bonded to the benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

Particularly, the constituent unit represented by general formula (1) is preferably at least one selected from the group consisting of the following formulas (5) to (7). Here, "comprising a constituent unit" or "having—as a constituent unit" means that a compound has one or more of the constituent unit. Such a constituent unit is preferably contained as a repeating unit in a tetralin ring-containing polyester compound. When the tetralin ring-containing polyester compound is a polymer, the polymer may be any of a homopolymer of the above constituent unit, a random copolymer of the above constituent unit and other constituent units, and a block copolymer of the above constituent unit and other constituent units.

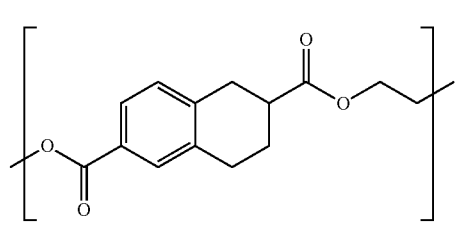 (5)

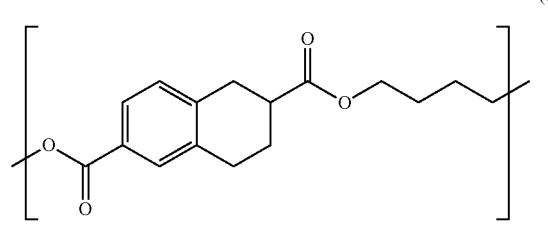 (6)

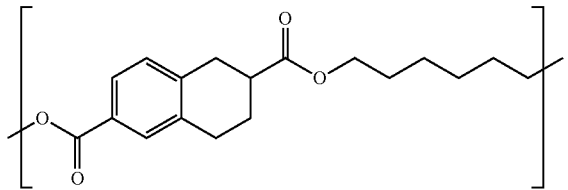

(7)

In the constituent unit represented by general formulas (1) to (4), examples of the monovalent substituent represented by R include, but are not limited to, a halogen atom (such as a chlorine atom, a bromine atom, and an iodine atom), an alkyl group (a linear, branched, or cyclic alkyl group preferably having 1 to 15 carbon atoms, more preferably 1 to 6 carbon atoms; such as a methyl group, an ethyl group, a n-propyl group, an isopropyl group, a tert-butyl group, a n-octyl group, a 2-ethylhexyl group, a cyclopropyl group, and a cyclopentyl group), an alkenyl group (a linear, branched, or cyclic alkenyl group preferably having 2 to 10 carbon atoms, more preferably 2 to 6 carbon atoms; such as a vinyl group and an allyl group), an alkynyl group (an alkynyl group preferably having 2 to 10 carbon atoms, more preferably 2 to 6 carbon atoms; such as an ethynyl group and a propargyl group), an aryl group (an aryl group preferably having 6 to 16 carbon atoms, more preferably 6 to 10 carbon atoms; such as a phenyl group and a naphthyl group), a heterocyclic group (a monovalent group obtained by removing one hydrogen atom from a 5-membered or 6-membered, aromatic or non-aromatic heterocyclic compound, preferably having 1 to 12 carbon atoms, more preferably 2 to 6 carbon atoms; such as a 1-pyrazolyl group, a 1-imidazolyl group, and a 2-furyl group), a cyano group, a hydroxy group, a carboxyl group, an ester group, an amide group, a nitro group, an alkoxy group (a linear, branched, or cyclic alkoxy group preferably having 1 to 10 carbon atoms, more preferably 1 to 6 carbon atoms; such as a methoxy group and an ethoxy group), an aryloxy group (an aryloxy group preferably having 6 to 12 carbon atoms, more preferably 6 to 8 carbon atoms; such as a phenoxy group), an acyl group (a formyl group is included. An alkylcarbonyl group preferably having 2 to 10 carbon atoms, more preferably 2 to 6 carbon atoms and an arylcarbonyl group preferably having 7 to 12 carbon atoms, more preferably 7 to 9 carbon atoms; such as an acetyl group, a pivaloyl group, and a benzoyl group), an amino group (an alkylamino group preferably having 1 to 10 carbon atoms, more preferably 1 to 6 carbon atoms, an anilino group preferably having 6 to 12 carbon atoms, more preferably 6 to 8 carbon atoms, and a heterocyclic amino group preferably having 1 to 12 carbon atoms, more preferably 2 to 6 carbon atoms; such as an amino group, a methylamino group, and an anilino group), a thiol group, an alkylthio group (an alkylthio group preferably having 1 to 10 carbon atoms, more preferably 1 to 6 carbon atoms; such as a methylthio group and an ethylthio group), an arylthio group (an arylthio group preferably having 6 to 12 carbon atoms, more preferably 6 to 8 carbon atoms; such as a phenylthio group), a heterocyclic thio group (a heterocyclic thio group preferably having 2 to 10 carbon atoms, more preferably 1 to 6 carbon atoms; such as a 2-benzothiazolylthio group), and an imide group (an imide group preferably having 2 to 10 carbon atoms, more preferably 4 to 8 carbon atoms; such as an N-succinimide group and an N-phthalimide group).

Note that when the above monovalent substituent R has a hydrogen atom, the hydrogen atom may be further replaced by a substituent T (here, the substituent T has the same meaning as that described in the above monovalent substituent R). Specific examples thereof include, but are not limited to, an alkyl group substituted with a hydroxy group (such as a hydroxyethyl group), an alkyl group substituted with an alkoxy group (such as a methoxyethyl group), an alkyl group substituted with an aryl group (such as a benzyl group), an alkyl group substituted with a primary amino group or a secondary amino group (such as an aminoethyl group), an aryl group substituted with an alkyl group (such as a p-tolyl group), and an aryloxy group substituted with an alkyl group (such as a 2-methylphenoxy group).

Note that when the above monovalent substituent R has a monovalent substituent T, the number of carbon atoms of the substituent T are not included in the number of carbon atoms described above. For example, a benzyl group is regarded as an alkyl group having one carbon atom substituted with a phenyl group, and is not regarded as an alkyl group having seven carbon atoms substituted with a phenyl group. Further, when the above monovalent substituent R has a substituent T, a plurality of the substituents T may be present.

X represents a divalent group having at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group. The aromatic hydrocarbon group, the saturated or unsaturated alicyclic hydrocarbon group, the linear or branched, saturated or unsaturated aliphatic hydrocarbon group, and the heterocyclic group may be substituted or unsubstituted. X may contain a hetero atom, and may contain an ether group, a sulfide group, a carbonyl group, a hydroxy group, an amino group, a sulfoxide group, a sulfone group, and the like. Examples of the aromatic hydrocarbon group include, but are not limited to, an o-phenylene group, a m-phenylene group, a p-phenylene group, a methylphenylene group, an o-xylylene group, a m-xylylene group, a p-xylylene group, a naphthylene group, an anthracenylene group, a phenanthrylene group, a biphenylene group, and a fluorenylene group. Examples of the alicyclic hydrocarbon group include, but are not particularly limited to, cycloalkylene groups such as a cyclopentylene group, a cyclohexylene group, a methylcyclohexylene group, a cycloheptylene group, and a cyclooctylene group, and cycloalkenylene groups such as cyclohexenylene group. Examples of the aliphatic hydrocarbon group include, but are not limited to, linear or branched alkylene groups such as a methylene group, an ethylene group, a trimethylene group, a propylene group, an isopropylidene group, a tetramethylene group, an isobutylene group, a tert-butylene group, a pentamethylene group, a hexamethylene group, a heptamethylene group, an octamethylene group, a nonamethylene group, and a decamethylene group, and alkenylene groups such as a vinylene group, a propenylene group, a 1-butenylene group, a 2-butenylene group, a 1,3-butadienylene group, a 1-pentenylene group, a 2-pentenylene group, a 1-hexenylene group, a 2-hexenylene group, and a 3-hexenylene group. These may further have a substituent, and specific examples thereof include, but are not limited to, a halogen atom, an alkoxy group, a hydroxy group, a carboxyl group, a carboalkoxy group, an acyl group, a thio group (such as an alkylthio group, a phenylthio group, a tolylthio group, and a pyridylthio group), an amino group (such as an unsubstituted amino group, a methylamino group, a dimethylamino group, and a phenylamino group), a cyano group, and a nitro group.

The polyester compound (a) comprising the constituent unit represented by general formula (1) can be produced, for example, by known methods. For example, it can be produced by polymerizing a tetralin dicarboxylic acid alkyl ester as a monomer.

A constituent unit which does not have a tetralin ring may also be incorporated into the polyester compound (a) of the present embodiment as a copolymerization component as long as that does not adversely affect performance. Specifically, compounds such as aliphatic dicarboxylic acids such as adipic acid and sebacic acid, benzene dicarboxylic acids such as terephthalic acid, and naphthalene dicarboxylic acids such as 2,6-naphthalene dicarboxylic acid can be used as other copolymerization components.

Preferred specific examples of the polyester compound (a) comprising the constituent unit represented by general formula (1) include, but are not limited to, those comprising the constituent units represented by the above formulas (5) to (7) and the following formulas (8) to (10). Among these, polyester compounds comprising the constituent unit represented by any of the formulas (5) to (7) are preferred.

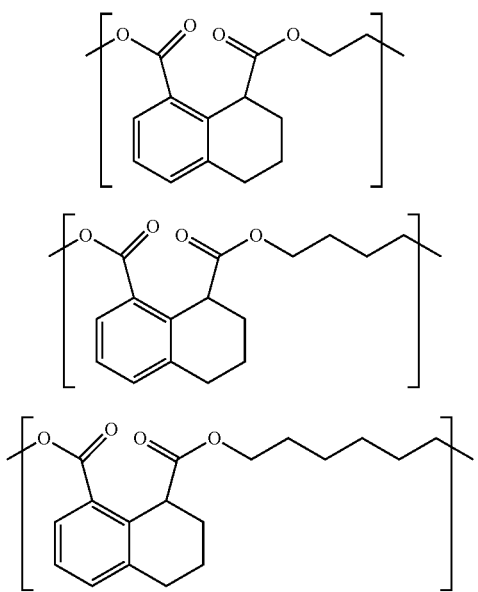

All of the above-described polyester compounds (a) have hydrogen at the benzylic position of the tetralin ring. When the polyester compound (a) is used in combination with a transition metal catalyst, hydrogen at the benzylic position is abstracted, thereby developing excellent oxygen-absorbing capacity (however, the mechanism of the present embodiment is not limited to these).

Further, the oxygen-absorbing resin composition as described above can also suppress the production of a low molecular weight compound after oxygen absorption. The reason is not clear, but, for example, the following oxidation reaction mechanism can be assumed. That is, it is assumed that, in the polyester compound (a), hydrogen at the benzylic position of the tetralin ring is first abstracted to produce a radical, and that then a carbon at the benzylic position is oxidized by the reaction of the radical with oxygen to produce a hydroxy group or a ketone group. Therefore, the followings are assumed: since the molecular chains are not cut by oxidation reaction as in the above prior art to thereby maintain the structure of the polyester compound (a) in the oxygen-absorbing resin composition of the present embodiment, a low molecular weight organic compound causing an odor is hardly produced after oxygen absorption; as a result, an increase in odor intensity after oxygen absorption is suppressed; and additionally, contamination of the low molecular weight compound into the contents is prevented (however, the mechanism of the present embodiment is not limited to these).

The intrinsic viscosity of the polyester compound (a) of the present embodiment (a measured value at 25° C. obtained by using a mixed solvent of phenol and 1,1,2,2-tetrachloroethane in a mass ratio of 6:4 (phenol:1,1,2,2-tetrachloroethane)) is not limited to, but is preferably 0.1 to 2.0 dL/g, more preferably 0.5 to 1.5 dL/g, from the point of view of the moldability of the polyester compound (a).

[Transition Metal Catalyst]

The transition metal catalyst used in the oxygen-absorbing resin composition of the present embodiment can be arbitrarily selected from known transition metal catalysts and is not particularly limited as long as it can serve as a catalyst of the oxidation reaction of the thermoplastic resin (a) having a tetralin ring as a constituent unit.

Specific examples of the transition metal catalyst include an organic acid salt, a halide, a phosphate, a phosphite, a hypophosphite, a nitrate, a sulfate, an oxide, a hydroxide, and the like of a transition metal. Here, examples of a transition metal contained in the transition metal catalyst include, but are not limited to, titanium, vanadium, chromium, manganese, iron, cobalt, nickel, copper, zinc, ruthenium, and rhodium. Among these, manganese, iron, cobalt, nickel, and copper are preferred. Further, examples of an organic acid include, but are not limited to, acetic acid, propionic acid, octanoic acid, lauric acid, stearic acid, acetylacetone, dimethyldithiocarbamic acid, palmitic acid, 2-ethyl hexanoic acid, neodecanoic acid, linoleic acid, tall oil acid, oleic acid, capric acid, and naphthenic acid. The transition metal catalyst is preferably obtained by combining these transition metals with organic acids, and more preferred are combinations of manganese, iron, cobalt, nickel, or copper as a transition metal with acetic acid, stearic acid, 2-ethyl hexanoic acid, oleic acid, or naphthenic acid as an organic acid. Note that the transition metal catalyst may be used singly or in combination of two or more.

The amount of the transition metal catalyst to be blended is not particularly limited, but can be arbitrarily set depending on the type and desired performance of the thermoplastic resin (a) and transition metal catalyst to be used. From the point of view of the amount of oxygen absorbed in the oxygen-absorbing resin composition, the amount of the transition metal catalyst to be blended is preferably 0.001 to 10 parts by mass, more preferably 0.002 to 2 parts by mass, further preferably 0.005 to 1 part by mass, in terms of the amount of a transition metal, based on 100 parts by mass of the polyester compound (a).

The thermoplastic resin (a) and the transition metal catalyst can be mixed by known methods, but are preferably kneaded with an extruder. Thereby, an oxygen-absorbing resin composition having good dispersibility can be obtained. Further, other additives, such as a drying agent, a pigment, a dye, an antioxidant, a slipping agent, an antistatic agent, a stabilizer; a filler such as calcium carbonate, clay, mica, and silica; and a deodorant, may be added to the oxygen-absorbing resin composition as long as that does not impair the effects of the present embodiment. However, other additives are not limited to those described above, but various materials may be used in combination.

Note that the oxygen-absorbing resin composition of the present embodiment may further contain a radical generator and a photoinitiator as needed in order to accelerate the oxygen absorption reaction. Further, the oxygen-absorbing resin composition of the present embodiment may also be kneaded with other thermoplastic resins in an extruder as long as that does not obstruct an object of the present embodiment. Known materials may be used as these radical generators, photoinitiators, and other thermoplastic resins. Examples of radical generators include N-hydroxy imide compounds such as N-hydroxy succinimide and N-hydroxy maleimide. Examples of photoinitiators include benzophenone and a derivative thereof, a thiazine dye, a metalloporphyrin derivative, an anthraquinone derivative. Examples of other thermoplastic resins include polyolefin typified by polyethylene, an ethylene-vinyl compound copolymer, a styrenic resin, a polyvinyl compound, polyamide, polyester, and polycarbonate.

[Oxygen-Absorbing Multilayer Body and Multilayer Container]

A sterilized oxygen-absorbing multilayer container can be obtained by using the above-described sterilized oxygen-absorbing resin composition. A suitable embodiment of a method for producing the same includes a method for producing a sterilized oxygen-absorbing multilayer container, the method comprising: a sterilizing step of irradiating with radiation an oxygen-absorbing multilayer container (before heating) comprising an oxygen-absorbing multilayer body, wherein the oxygen-absorbing multilayer body comprises at least an oxygen absorbing layer (layer A) comprising an oxygen-absorbing resin composition comprising a transition metal catalyst and a thermoplastic resin (a) having a tetralin ring as a constituent unit and a layer (layer B) comprising a thermoplastic resin (b) formed on the oxygen absorbing layer (layer A); and, after the sterilizing step, a step of heating the oxygen-absorbing multilayer container at a temperature equal to or higher than the glass transition temperature of the thermoplastic resin (a) and equal to or lower than 200° C. According to the production method, even if the oxygen-absorbing multilayer container is colored by radiation irradiation, the coloration can be faded in a short time by heating the composition at a specific temperature of equal to or higher than the glass transition temperature of the thermoplastic resin (a) and equal to or lower than 200° C. That is, sufficient sterilization treatment can be performed, and the coloration of the container can be effectively suppressed. In addition, since plastic deformation and the like by heating can be effectively suppressed by laminating the layer B to the layer A (oxygen absorbing layer), moldability can be further improved. Note that, although the details of the thermoplastic resin (b) will be described below, $Tg_{(b)}$ of the thermoplastic resin (b) is preferably higher than the $Tg_{(a)}$ of the layer A ($Tg_{(a)} < Tg_{(b)}$) from the point of view of moldability.

Then, examples of a suitable embodiment of the sterilized oxygen-absorbing multilayer container include a sterilized oxygen-absorbing multilayer container obtained by performing at least a sterilizing step of irradiating with radiation an oxygen-absorbing multilayer container comprising an oxygen-absorbing multilayer body, wherein the oxygen-absorbing multilayer body comprises at least two layers of an oxygen absorbing layer (layer A) comprising an oxygen-absorbing resin composition comprising a thermoplastic resin (a) and a transition metal catalyst, and a layer (layer B) comprising a thermoplastic resin (b) formed on the oxygen absorbing layer (layer A); and, after the sterilizing step, a step of heating the oxygen-absorbing multilayer container at a temperature equal to or higher than the glass transition temperature (Tg) of the thermoplastic resin (a) and equal to or lower than 200° C.

The oxygen-absorbing multilayer body comprises at least two layers of the above-described oxygen absorbing layer (layer A) and layer (layer B) comprising a thermoplastic resin (b) (A/B). Further, the oxygen-absorbing multilayer container of the present embodiment comprises the above-described oxygen-absorbing multilayer body.

The layer constitution of the oxygen-absorbing multilayer body is not particularly limited, and the number and the type of the layer A and the layer B are not particularly limited. For example, the layer constitution may be an A/B structure consisting of one layer A and one layer B, or may be a three-layer constitution of B/A/B consisting of one layer A and two layer Bs. Further, the layer constitution may be a five-layer constitution of B1/B2/A/B2/B1 consisting of one layer A and four layer Bs consisting of two types of layers: layer B1 and layer B2. Furthermore, the multilayer body of the present embodiment may also have an arbitrary layer such as an adhesive layer (layer AD) as needed. For example, the multilayer body may be a seven-layer constitution of B1/AD/B2/A/B2/AD/B1.

A preferred embodiment includes an oxygen-absorbing multilayer container, wherein the oxygen-absorbing multilayer container comprises an oxygen-absorbing multilayer body having three or more layers, the oxygen-absorbing multilayer body comprising at least an oxygen absorbing layer (layer A), a layer (layer B1) comprising a thermoplastic resin (b1) formed on one surface of the oxygen absorbing layer (layer A), and a layer (layer B2) comprising a thermoplastic resin (b2) formed on the other surface of the oxygen absorbing layer (layer A); and the heating temperature of the heating step is equal to or higher than the glass transition temperature of the thermoplastic resin (a) and equal to or lower than either the glass transition temperature of the thermoplastic resin (b1) or the glass transition temperature of the thermoplastic resin (b2). This embodiment is an embodiment having at least three layers of layer B1/layer A/layer B2, in which plastic deformation during heating can be suppressed much more effectively by using, as outside layers, layers of thermoplastic resins each having a Tg higher than the Tg of the layer A which is an intermediate layer. As a result, moldability is further improved. From such a point of view, the heating temperature of the heating step described above is preferably equal to or higher than the glass transition temperature of the thermoplastic resin (a) and equal to or lower than both the glass transition temperature of the thermoplastic resin (b1) and the glass transition temperature of a thermoplastic resin (b2). That is, the heating temperature is preferably equal to or lower than either the $Tg_{(b1)}$ of the layer B1 or the $Tg_{(b2)}$ of the layer B2, more preferably equal to or lower than both the $Tg_{(b1)}$ of the layer B1 and the $Tg_{(b2)}$ of the layer b2. For example, when the $Tg_{(b1)}$ of the layer B1 is lower than the $Tg_{(b2)}$ of the layer B2 ($Tg_{(b1)} < Tg_{(b2)}$), the heating temperature is preferably lower than the $Tg_{(b2)}$ of the layer B2, more preferably lower than the $Tg_{(b1)}$ of the layer B1. In this embodiment, the $Tg_{(b1)}$ of the layer B1 and the $Tg_{(b2)}$ of the layer B2 are preferably 80 to 200° C., more preferably 90 to 180° C., further preferably 100 to 160° C. Generally, when the thermoplastic resin having a Tg in such a temperature range is used, the plastic deformation during heating described above tends to be able to be much more efficiently suppressed, and the excellent moldability can be maintained, by the relationship with the $Tg_{(a)}$ of the thermoplastic resin (a) of the layer A.

[Oxygen Absorbing Layer (Layer A)]

The oxygen absorbing layer (layer A) of the present embodiment comprises an oxygen-absorbing resin composition comprising a transition metal catalyst and a thermoplastic resin (a) having a tetralin ring as a constituent unit.

The content of the thermoplastic resin (a) in the layer A is not particularly limited, but is preferably 50 to 100% by mass, more preferably 70 to 100% by mass, further preferably 90 to 100% by mass. The oxygen-absorbing performance can be further increased by controlling the content of the thermoplastic resin (a) in the above range.

The thickness of the oxygen absorbing layer (layer A) is not particularly limited, but is preferably 1 to 1000 μm, more preferably 2 to 800 μm, further preferably 5 to 700 μm. The oxygen absorbing properties of the layer A can be further increased, and the economical efficiency can be prevented from being impaired, by controlling the thickness of the layer A in the above range.

[Layer (Layer B), (Layer B1), (Layer B2) Comprising Thermoplastic Resin (b), (b1), (b2), Respectively]

The layer B of the present embodiment is a layer comprising a thermoplastic resin (b). Note that the layer B is generically referred to as "layer B" including the layer B1 and the layer B2 described above, unless otherwise specified. Similarly, the thermoplastic resin (b) is generically referred to as a "thermoplastic resin (b)" including the thermoplastic resin (b1) and the thermoplastic resin (b2). The thermoplastic resin (b) is a thermoplastic resin other than the thermoplastic resin (a). The content of the thermoplastic resin (b) in the layer B is not particularly limited, but is preferably 70 to 100% by mass, more preferably 80 to 100% by mass, further preferably 90 to 100% by mass. Note that, in the case of an embodiment in which there are a plurality of thermoplastic resin layers, such as the layers B1 and B2, the content of the thermoplastic resin (b) in the layer B as described here refers to the content of a thermoplastic resin in each layer.

The oxygen-absorbing multilayer container of the present embodiment may have a plurality of layer Bs, such as the layers B1 and B2 as described above. When the oxygen-absorbing multilayer container has a plurality of layer Bs, the constitution of the layer B may be the same or different from each other. The thickness of the layer B may be arbitrarily determined depending on applications. Generally, from the point of view of securing various physical properties such as flexibility and strength such as drop resistance required for multilayer containers, the thickness is preferably 5 to 1000 μm, more preferably 10 to 800 μm, further preferably 20 to 500 μm.

Any thermoplastic resins other than the thermoplastic resin (a) can be used as the thermoplastic resin (b) without limitation. Specific examples of the thermoplastic resin (b) include known resins such as polyolefin, polyester, polyamide, an ethylene-vinyl alcohol copolymer, a plant-derived resin, and a chlorine-based resin. The thermoplastic resin (b) preferably includes at least one selected from the group consisting of these resins. Among these, polyolefin is preferred. More specific suitable examples include a copolymer in which norbornene and an olefin such as ethylene are used as raw materials; and a cycloolefin copolymer (COC) which is a copolymer in which tetracyclododecene and an olefin such as ethylene are used as raw materials. Further, a cycloolefin polymer (COP) is also particularly preferred, which is a polymerized product obtained by ring opening polymerization of norbornene followed by hydrogenation. Those described, for example, in Japanese Patent Laid-Open No. 5-300939 and Japanese Patent Laid-Open No. 5-317411 can also be used as these COC and COP.

A commercially available product can be used as COC. For example, it is commercially available as APEL (trade name) manufactured by Mitsui Chemicals, Inc. A commercially available product can be used as COP. For example, it is commercially available as ZEONEX (trade name) or ZEONOR (trade name) manufactured by Zeon Corporation and Daikyo Resin CZ (trade name) manufactured by Daikyo Seiko, Ltd. The COC and COP are particularly preferred materials because they exhibit chemical properties such as heat resistance and light resistance, chemical resistance (which are the feature derived from a polyolefin resin), and physical properties such as mechanical properties, fusion characteristics, flow properties and dimension accuracy (which are features derived from an amorphous resin).

The oxygen-absorbing multilayer body may further have arbitrary layers depending on desired performance and the like, in addition to the oxygen absorbing layer (layer A) and the layer comprising the thermoplastic resin (b) (layer B). Examples of such an arbitrary layer include an adhesive layer (layer AD). For example, in a constitution in which the layer B is formed on the layer A, the constitution may be a constitution in which the layer B is formed on the layer A with the layer AD between them (layer A/layer AD/layer B).

In an oxygen-absorbing multilayer body, when practical interlayer adhesion strength between adjacent two layers is not obtained, it is preferred to provide an adhesive layer (layer AD) between these two layers. The adhesive layer preferably contains a thermoplastic resin having adhesive properties. Examples of the thermoplastic resin having adhesive properties include acid-modified polyolefin resins in which a polyolefin-based resin such as polyethylene or polypropylene is modified with an unsaturated carboxylic acid such as acrylic acid, methacrylic acid, maleic acid, maleic anhydride, fumaric acid, or itaconic acid; and polyester-based thermoplastic elastomers having a polyester-based block copolymer as the main component. In the adhesive layer, it is preferred to use a resin obtained by modifying a resin of the same type as the thermoplastic resin used for the layer B from the point of view of adhesive properties. From the point of view of securing molding processability while exhibiting practical adhesive strength, the thickness of the adhesive layer is preferably 2 to 100 μm, more preferably 5 to 90 μm, further preferably 10 to 80 μm.

The production method and the layer constitution of the sterilized oxygen-absorbing multilayer container of the present embodiment is not particularly limited, but can be produced by a common injection molding process.

For example, a material forming the layer A and a material forming the layer B can be injected into a cavity from each injection cylinder through a mold hot runner using a molding machine equipped with two or more injection machines and an injection mold to produce a multilayer container corresponding to the shape of the injection mold.

Further, a material forming the layer B is first injected from an injection cylinder; a material forming the layer A is then injected from a separate injection cylinder simultaneously with the resin forming the layer B; and then a required amount of the resin forming the layer B is injected to fill a cavity, thus capable of producing a multilayer container having a three-layer constitution of B/A/B.

Further, a material forming the layer B is first injected; a material forming the layer A is individually injected; and a required amount of the material forming the layer B is finally injected to fill a mold cavity, thus capable of producing a multilayer container having a five-layer constitution of B/A/B/A/B.

Further, a material forming the layer B1 is first injected from an injection cylinder; a material forming the layer B2 is then injected from a separate injection cylinder simultaneously with the resin constituting the layer B1; a resin forming the layer A is then injected simultaneously with the resins forming the layer B1 and the layer B2; and a required amount of the resin forming the layer B1 is then injected to fill a cavity, thus capable of producing a multilayer container having a five-layer constitution of B1/B2/A/B2/B1.

Further, a multilayered molded product may be obtained by a compression molding process instead of an injection molding process. For example, a molded product can be obtained by providing an oxygen-absorbing resin agent in a thermoplastic resin molten material, feeding the molten lump to a male mold, compressing the molten lump with a female mold, and cooling and solidifying the compression molded material.

In order to give heat resistance to a top neck part of the molded product obtained, the top neck part may be crystallized by heat treatment at this stage. The degree of crystallinity is preferably 30 to 50%, more preferably 35 to 45%. Note that the crystallization may be performed after the secondary fabrication to be described below is performed.

Further, materials may be formed into a desired container shape by molding means such as extrusion molding and compression molding (sheet molding, blow molding).

Examples of the shape of the oxygen-absorbing multilayer container of the present embodiment include, but are not limited to, a bag, a tray, a cup, a bottle, a tube, PTP (a press through pack, also referred to as a blister), a vial, an ampoule, a prefilled syringe, and a vacuum blood collecting tube.

[Sterilization Treatment with Radiation]

The sterilization treatment with radiation of the present embodiment is performed by irradiating with at least one selected from gamma rays and X-rays classified as electromagnetic waves; and electron beams classified as particle beams. The gamma rays that can be used in the above gamma irradiation generally include, but are not limited to, gamma rays emitted from a $Co^{60}$ radiation source which is a radioisotope of Co. Further, X-rays that can be used in the above X-ray irradiation generally include, but are not limited to, X-rays generated by applying electron beams accelerated in a X-ray tube or a Crookes tube using Cu, Mo, W, or the like as an anticathode. Further, electron beams that can be used in the above electron beam irradiation generally include, but are not limited to, electron beams having an energy of 150 to 10000 KeV emitted from various electron beam accelerators such as a Cockcroft-Walton type, a Van der Graaff type, a resonance transformer type, an insulated core transformer type, a linear accelerator, an electrostatic accelerator, a Dynamitron type, and a high frequency cyclotron.

In the radiation irradiation of the present embodiment, the dose of the radiation to be irradiated is not particularly limited, but is preferably 1 kGy to 200 kGy, more preferably 10 kGy to 150 kGy, further preferably 20 kGy to 100 kGy, further more preferably 20 kGy to 55 kGy, from the point of view of suppressing the degradation of resin.

The timing of performing the sterilization treatment with radiation to the oxygen-absorbing resin composition is not limited at all, but it is preferred to perform the sterilization treatment with radiation after the preparation of the multilayer container from the point of view of reducing the contamination risk after the sterilization treatment with radiation.

Since the oxygen-absorbing resin composition of the present embodiment and the multilayer container using the same are colored after the sterilization treatment with radiation, the information that the sterilization treatment has been performed or not can be confirmed by checking the color before the heat treatment to be described below. That is, the coloration can be utilized as an indicator of the sterilization treatment with radiation.

[Heat Treatment]

The coloration of the oxygen-absorbing resin composition and the oxygen-absorbing multilayer container generated by the sterilization treatment with radiation can be faded by performing heat treatment of the present embodiment. The heating is performed in an atmosphere including, but not limited to, inert gas such as nitrogen, carbon dioxide, and argon, air, vacuum, and water. The devices used for heat treatment are not limited at all, but known devices can be used, and examples thereof include an air forced oven. The heating temperature is not limited at all as long as it is equal to or higher than the glass transition temperature (Tg) of the thermoplastic resin (a) and equal to or lower than 200° C., preferably equal to or lower than 180° C., more preferably equal to or lower than 150° C., further more preferably equal to or lower than 120° C. The fading of the coloration by radiation irradiation is slow if the heating temperature is less than the Tg of the thermoplastic resin (a). Further, if the heating temperature is higher than 200° C., the degradation of the oxygen-absorbing resin composition or the oxygen-absorbing multilayer container by heat will be remarkable. Therefore, such a temperature is not preferred. Further, the degradation of the oxygen-absorbing resin composition or the oxygen-absorbing multilayer container by heat can be suppressed by setting the heating temperature to a value equal to or lower than the above preferred values.

In the heat treatment of the present embodiment, the heating time is not limited at all, but from the point of view of the fading effect of coloration by heat treatment and the cost, the heating time is preferably 1 minute to 120 minutes, more preferably 5 minutes to 80 minutes, further preferably 10 minutes to 60 minutes. Further, although heat treatment is performed after sterilization treatment with radiation, the timing is not limited at all. The heat treatment may be performed immediately after the sterilization treatment with radiation or may be performed after a specified time lapse.

The oxygen-absorbing resin composition of the present embodiment and the multilayer container using the same are excellent in the oxygen-absorbing performance in a wide humidity conditions from low humidity to high humidity (a relative humidity of 0% to 100%) because water is not required for oxygen absorption, and are suitable for the packaging of various articles because they are excellent in the flavor maintenance of contents. Specific examples of materials to be stored include, but are not limited to, various articles such as beverages such as milk, juice, coffee, tea, and an alcoholic beverage; liquid seasonings such as sauce, soy sauce, and dressing; cooked foods such as soup, a stew, and curry; pasty foods such as jam and mayonnaise; fishery products such as tuna and fish and shellfish; dairy processed goods such as cheese and butter; meat processed goods such as meat, salami, sausage, and ham; vegetables such as carrots and potatoes; eggs; noodles; processed rice products such as rice before cooking, cooked rice, and rice porridge; dried foods such as powder seasoning, powder coffee, powdered milk for infants, cooked foods for infants, powdered diet foods, cooked foods for care, dried vegetables, and rice crackers; chemical products such as pesticide and insecticide; drugs; pet foods; and detergent. Particularly, the oxygen-absorbing resin composition of the present embodiment and the multilayer container using the same are suitable as packaging media for the contents that easily cause degradation in the presence of oxygen, such as beverages such as beer, wine, fruit juice, and a carbonated soft drink; foods such as fruit, nuts, vegetables, processed meat, small child's foods, coffee, jam, mayonnaise, catsup, cooking oil, dressing, sauce, foods boiled down with soy sauce, and dairy products; and drugs and cosmetics.

EXAMPLES

Hereinafter, the present invention will be described in detail with reference to Examples and Comparative Examples, but the present invention is not limited to these. Note that NMR measurement was performed at room temperature using "AVANCE 111-500" manufactured by BRUKER GmbH unless otherwise stated.
[Synthesis Example of Monomer]
An autoclave having an internal volume of 18 L was charged with 2.20 kg of naphthalene-2,6-dicarboxylic acid dimethyl ester, 11.0 kg of 2-propanol, and 350 g of a catalyst (containing water in an amount of 50% by weight) in which palladium is supported by activated carbon in an amount of 5%. Next, the air in the autoclave was replaced with nitrogen; the nitrogen was replaced with hydrogen; and then hydrogen was fed to the autoclave until the pressure therein reached 0.8 MPa. Then, a stirrer was started; the rotational speed thereof was adjusted to 500 rpm; the internal temperature was increased to 100° C. over 30 minutes; and hydrogen was further fed to bring the pressure to 1 MPa. Subsequently, the feeding of hydrogen was continued so as to maintain 1 MPa depending on the decrease of pressure due to the progress of reaction. Since the pressure decrease stopped after 7 hours, the autoclave was cooled, and unreacted residual hydrogen was released. Then, a reaction mixture was removed from the autoclave. The reaction mixture was filtered to remove the catalyst, and then 2-propanol was evaporated from the separated filtrate by an evaporator to obtain a crude product. To the resulting crude product was added 4.40 kg of 2-propanol, and the crude product was purified by recrystallization to obtain tetralin-2,6-dicarboxylic acid dimethyl ester at a yield (a yield based on naphthalene-2,6-dicarboxylic acid dimethyl ester) of 80%. Note that NMR analysis results were as described below. $^1$H-NMR (400 MHz CDCl$_3$) δ7.76-7.96 (2H m), 7.15 (1H d), 3.89 (3H s), 3.70 (3H s), 2.70-3.09 (5H m), 1.80-1.95 (1H m).
[Production Example of Polymer]
An apparatus for producing a polyester resin equipped with a packed column type rectifier, a partial condenser, a total condenser, a cold trap, a stirrer, a heating device, and a nitrogen introducing tube was charged with 543 g of tetralin-2,6-dicarboxylic acid dimethyl ester obtained in the synthesis example of monomer, 217 g of ethylene glycol, and 0.171 g of tetrabutyl titanate and heated to 230° C. in a nitrogen atmosphere to perform transesterification reaction. The reaction conversion of the dicarboxylic acid component was increased to 85% or more, and then thereto was added 0.171 g of tetrabutyl titanate. The resulting mixture was gradually heated and decompressed and subjected to polycondensation at 245° C. and 133 Pa or less to obtain a polyester compound (1) having a structure represented by the following formula (5).

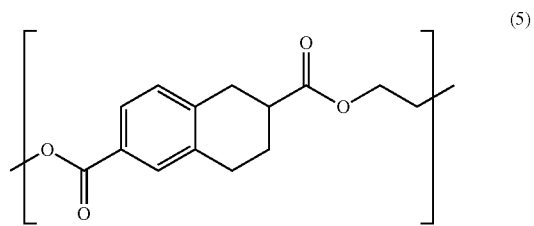

(5)

The weight average molecular weight and the number average molecular weight of the resulting polyester compound (1) were measured by gel permeation chromatography (GPC). As a result, the weight average molecular weight in terms of polystyrene was $8.5 \times 10^4$, and the number average molecular weight was $3.0 \times 10^4$. Note that the measurement conditions of GPC were as follows.
Measurement device: "HLC-8320GPC EcoSEC" manufactured by Tosoh Corporation
Columns used: "TSKgel SuperH2000", "TSKgel SuperHM-L", and "TSKgel SuperHSO00" manufactured by Tosoh Corporation
Solvent of mobile phase: Chloroform
Temperature: 40° C.
Flow rate: 0.6 mL/min
As a result of measuring glass transition temperature and a melting point using a differential scanning calorimeter (DSC), the glass transition temperature was 67° C., and the melting point were not observed since the compound was amorphous. Note that the measurement conditions of DSC were as follows.
Measurement device: "DSC-60" manufactured by Shimadzu Corporation
Measurement start temperature: 25° C.
Heating rate: 10° C./min
Arrival temperature: 220° C.
Cooling rate: 5° C./min Example 1-1

An oxygen-absorbing resin composition was obtained by dry-blending cobalt (II) stearate with 100 parts by mass of the polyester compound (1) such that the amount of cobalt was adjusted to 0.02 part by mass. An oxygen-absorbing film having a width of 130 mm and a thickness of 245 to 255 μm was prepared by film-forming the oxygen-absorbing resin composition under the conditions of an extrusion temperature of 220° C., a screw rotation speed of 60 rpm, a feed screw rotation speed of 16 rpm, and a haul-off speed of 1.3 m/min, using a twin-screw extruder having two screws each having a diameter of 20 mm. Then, a test piece (100 mm in length×100 mm in width) of the resulting oxygen-absorbing film was irradiated (irradiation time: 5 hours) in air at room temperature with 50 kGy of gamma rays emitted from a Co$^{60}$ radiation source.
Next, the test piece irradiated with gamma rays was put in an automatic oven (model: DS400, manufactured by Yamato Scientific Co., Ltd.) and subjected to heat treatment for 15 minutes at 80° C. in air. Subsequently, the film was cooled to room temperature and then measured for yellowness (Yellow Index: YI). Further, the film after the gamma irradiation and heat treatment was stored for one week at 23° C. and 50% RH and then measured for YI. A color-difference and turbidity measuring device (model: COH-400, manufactured by Nippon Denshoku Industries Co., Ltd.) was used for the YI measurement. The results are shown in Table 1.

Examples 1-2 to 1-12

Examples 1-2 to 1-12 were performed in the same manner as in Example 1-1 except that the gamma irradiation dose, heating temperature, and heating time were changed as shown in Table 1, and the oxygen-absorbing films were measured for YI. The results are shown in Table 1.

Example 1-13

A test piece (100 mm in length x 100 mm in width) of the oxygen-absorbing film prepared in the same manner as in Example 1-1 was irradiated (irradiation time: 5 hours) in air at room temperature with 50 kGy of electron beams emitted from an electron beam generator using an electrostatic accelerator.

Next, the test piece irradiated with electron beams was put in an automatic oven (model: DS400, manufactured by Yamato Scientific Co., Ltd.) and subjected to heat treatment for 15 minutes at 80° C. in air. Subsequently, the film was cooled to room temperature and then measured for YI. Further, the film after the electron beam irradiation and heat treatment was stored for one week at 23° C. and 50% RH and then measured for YI. The results are shown in Table 1.

Examples 1-14 to 1-18

Examples 1-14 to 1-18 were performed in the same manner as in Example 1-13 except that the electron beam irradiation dose, heating temperature, and heating time were changed as shown in Table 1, and the oxygen-absorbing films were measured for YI. The results are shown in Table 1.

Comparative Example 1-1

Comparative Example 1-1 was performed in the same manner as in Example 1-1 except that heat treatment was not performed, and the oxygen-absorbing films were measured for YI. The results are shown in Table 1.

Comparative Example 1-2

Comparative Example 1-2 was performed in the same manner as in Comparative Example 1-1 except that the dose was set to 25 kGy, and the oxygen-absorbing films were measured for YI. The results are shown in Table 1.

Comparative Example 1-3

Comparative Example 1-3 was performed in the same manner as in Example 1-13 except that heat treatment was not performed, and the oxygen-absorbing films were measured for YI. The results are shown in Table 1.

Comparative Example 1-4

Comparative Example 1-4 was performed in the same manner as in Comparative Example 1-3 except that the dose was set to 25 kGy, and the oxygen-absorbing film were measured for YI. The results are shown in Table 1.

Comparative Example 1-5

Comparative Example 1-5 was performed in the same manner as in Example 1-1 except that heating temperature was set to 50° C., and the oxygen-absorbing films were measured for YI. The results are shown in Table 1.

TABLE 1

| | Type of radiation/ dose (kGy) | | Heating conditions | | YI of film (values inside the parentheses[1] are ΔYI) | | | |
|---|---|---|---|---|---|---|---|---|
| | Gamma rays | Electron beams | Temperature/ ° C. | Time/ min | Before radiation irradiation | After radiation irradiation/ before heat treatment | After heat treatment | One week after radiation irradiation |
| Example 1-1 | 50 | — | 80 | 15 | 0.1 (0) | 12.6 (+12.5) | 3.7 (+3.6) | 3.2 (+3.1) |
| Example 1-2 | 50 | — | 80 | 5 | −0.2 (0) | 12.2 (+12.4) | 6.2 (+6.4) | 5.4 (+5.6) |
| Example 1-3 | 50 | — | 80 | 30 | 0.2 (0) | 12.7 (+12.5) | 3.4 (+3.2) | 2.9 (+2.7) |
| Example 1-4 | 50 | — | 100 | 15 | 0.0 (0) | 12.5 (+12.5) | 3.3 (+3.3) | 2.8 (+2.8) |
| Example 1-5 | 50 | — | 100 | 5 | 0.1 (0) | 12.7 (+12.6) | 5.8 (+5.7) | 5.1 (+5.0) |
| Example 1-6 | 50 | — | 100 | 30 | 0.0 (0) | 12.5 (+12.5) | 3.1 (+3.1) | 2.6 (+2.6) |
| Example 1-7 | 25 | — | 80 | 15 | 0.1 (0) | 8.4 (+8.3) | 2.8 (+2.7) | 2.4 (+2.3) |
| Example 1-8 | 25 | — | 80 | 5 | −0.1 (0) | 8.1 (+8.2) | 3.5 (+3.6) | 3.0 (+3.1) |
| Example 1-9 | 25 | — | 80 | 30 | 0.3 (0) | 8.5 (+8.2) | 2.8 (+2.5) | 2.4 (+2.1) |
| Example 1-10 | 25 | — | 100 | 15 | −0.2 (0) | 8.0 (+8.2) | 2.4 (+2.6) | 1.9 (+2.1) |
| Example 1-11 | 25 | — | 100 | 5 | 0.1 (0) | 8.4 (+8.3) | 3.3 (+3.2) | 2.7 (+2.6) |
| Example 1-12 | 25 | — | 100 | 30 | 0.2 (0) | 8.6 (+8.4) | 2.8 (+2.6) | 2.4 (+2.2) |
| Example 1-13 | — | 50 | 80 | 15 | 0.0 (0) | 11.7 (+11.7) | 3.3 (+3.3) | 2.7 (+2.7) |
| Example 1-14 | — | 50 | 80 | 5 | 0.1 (0) | 11.8 (+11.7) | 5.9 (+5.8) | 5.1 (+5.0) |
| Example 1-15 | — | 50 | 80 | 30 | −0.1 (0) | 11.5 (+11.6) | 2.9 (+3.0) | 2.3 (+2.4) |
| Example 1-16 | — | 25 | 80 | 15 | 0.2 (0) | 7.8 (+7.6) | 2.8 (+2.6) | 2.4 (+2.2) |
| Example 1-17 | — | 25 | 80 | 5 | 0.1 (0) | 7.6 (+7.5) | 3.4 (+3.3) | 2.9 (+2.8) |
| Example 1-18 | — | 25 | 80 | 30 | 0.0 (0) | 7.5 (+7.5) | 2.5 (+2.5) | 2.0 (+2.0) |
| Comparative Example 1-1 | 50 | — | — | — | 0.1 (0) | 12.6 (+12.5) | — | 10.7 (+10.6) |
| Comparative Example 1-2 | 25 | — | — | — | −0.1 (0) | 8.3 (+8.4) | — | 7.1 (+7.2) |
| Comparative Example 1-3 | — | 50 | — | — | 0.2 (0) | 11.9 (+11.7) | — | 10.3 (+10.1) |
| Comparative Example 1-4 | — | 25 | — | — | 0.0 (0) | 7.5 (+7.5) | — | 6.7 (+6.7) |
| Comparative Example 1-5 | 50 | — | 50 | 15 | 0.1 (0) | 12.4 (+12.3) | 9.8 (+9.7) | 9.1 (+9.0) |

[1]Based on values before radiation irradiation

As described above, it was verified that, by performing heat treatment after radiation irradiation, the YI of a film of each Example more greatly decreased than the YI of a film of each Comparative Example, and the low YI was maintained thereafter. That is, it was at least verified that the implementation of heat treatment is very effective for fading the coloration due to radiation irradiation in a short time.

[Production Example of Multilayer Container (Vial)]

An injection-molded product having a three-layer constitution of B/A/B was obtained under the following conditions by injecting a material forming the layer B from an injection cylinder, then injecting a material forming the layer A from a separate injection cylinder simultaneously with the resin forming the layer B, and then injecting a required amount of the resin forming the layer A to fill a cavity in an injection mold. Then, the injection-molded product was cooled to a predetermined temperature, transferred to a blow mold, and then subjected to blow molding to produce a vial (bottle part). The total mass of the vial was set to 24 g, and the proportion (content) of the layer A was set to 30% by mass of the total mass of the vial. A cycloolefin polymer (COP, manufactured by Zeon Corporation, trade name "ZEONEX 690R", glass transition temperature (Tg) 136° C., total light transmittance (ASTM D1003, 3 mm in thickness) 92%) was used as a resin forming the layer B.

(Shape of Vial)

The total length was set to 89 mm; the outer diameter was set to 40 mm φ; and the thickness was set to 1.8 mm. Note that an integrated injection blow molding machine (manufactured by UNILOY, model: IBS 85, providing four vials) was used for producing the vial.

(Molding Conditions for Vial)

Injection cylinder temperature for layer A: 260° C.

Injection cylinder temperature for layer B: 280° C.

Temperature of resin flow channel in injection mold: 280° C.

Blow temperature: 150° C.

Temperature of cooling water for blow mold: 15° C.

[Evaluation of Vial]

The vials obtained in Examples and Comparative Examples were measured and evaluated for the oxygen transmission rate according to the following method.

Oxygen Transmission Rate (OTR) of Vial

A molded product was stored in an atmosphere of a temperature of 23° C., a relative humidity outside the molded product of 50%, and a relative humidity inside the molded product of 100%, and measured for the oxygen transmission rate on the 30th day from the start of the experiment. An oxygen transmission rate measurement apparatus (manufactured by MOCON, Inc., trade name "OX-TRAN 2-21 ML") was used for the measurement. It means that the lower the measured value becomes, the better the oxygen barrier property becomes. Note that the minimum limit of detection of the measurement is an oxygen transmission rate of $5 \times 10^{-5}$ mL/(0.21 atm·day·package).

Example 2-1

An oxygen-absorbing resin composition was obtained by dry-blending cobalt (II) stearate with 100 parts by mass of the polyester compound (1) such that the amount of cobalt was adjusted to 0.02 part by mass, feeding the blended material to a twin-screw extruder having two screws each having a diameter of 37 mm at a feeding rate of 30 kg/h, melt-kneading the material at a cylinder temperature of 220° C., extruding a strand from an extruder head, cooling the strand, and then pelletizing the cooled strand. A vial was produced using the oxygen-absorbing resin composition as a resin forming the layer A. Then, the resulting oxygen-absorbing multilayered vial was irradiated (irradiation time: about 5 hours) in air at room temperature with 50 kGy of gamma rays emitted from a $Co^{60}$ radiation source. Next, the vial irradiated with gamma rays was put in an automatic oven (model: DS400, manufactured by Yamato Scientific Co., Ltd.) and subjected to heat treatment for 15 minutes at 80° C. in air. Subsequently, the vial was cooled to room temperature and then measured for YI and the oxygen transmission rate in the same manner as in Example 1-1. Further, the multilayered vial after the gamma irradiation and heat treatment was stored for one week at 23° C. and 50% RH and then measured for YI. The results are shown in Table 2.

Examples 2-2 to 2-12

Examples 2-2 to 2-12 were performed in the same manner as in Example 2-1 except that the gamma irradiation dose, heating temperature, and heating time were changed as shown in Table 2, and the oxygen-absorbing multilayered vials were measured for YI and the oxygen transmission rate. The results are shown in Table 2.

Example 2-13

The oxygen-absorbing multilayered vial prepared in the same manner as in Example 2-1 was irradiated (irradiation time: 5 hours) in air at room temperature with 50 kGy of electron beams emitted from an electron beam generator using an electrostatic accelerator. Next, the vial irradiated with electron beams was put in an automatic oven (model: DS400, manufactured by Yamato Scientific Co., Ltd.) and subjected to heat treatment for 15 minutes at 80° C. in air. Subsequently, the vial was cooled to room temperature and then measured for YI and the oxygen transmission rate. Further, the multilayered vial after the electron beam irradiation and heat treatment was stored for one week at 23° C. and 50% RH and then measured for YI. The results are shown in Table 2.

Examples 2-14 to 2-18

Examples 2-14 to 2-18 were performed in the same manner as in Example 2-13 except that the electron beam irradiation dose, heating temperature, and heating time were changed as shown in Table 2, and the oxygen-absorbing multilayered vials were measured for YI and the oxygen transmission rate. The results are shown in Table 2.

Comparative Example 2-1

Comparative Example 2-1 was performed in the same manner as in Example 2-1 except that heat treatment was not performed, and the vials were measured for YI and the oxygen transmission rate. The results are shown in Table 2.

Comparative Example 2-2

Comparative Example 2-2 was performed in the same manner as in Comparative Example 2-1 except that the dose was set to 25 kGy, and the oxygen-absorbing multilayered vials were measured for YI and the oxygen transmission rate. The results are shown in Table 2.

Comparative Example 2-3

Comparative Example 2-3 was performed in the same manner as in Example 2-13 except that heat treatment was not performed, and the vials were measured for YI and the oxygen transmission rate. The results are shown in Table 2.

Comparative Example 2-4

Comparative Example 2-4 was performed in the same manner as in Comparative Example 2-3 except that the dose was set to 25 kGy, and the oxygen-absorbing multilayered vials were measured for YI and the oxygen transmission rate. The results are shown in Table 2.

Comparative Example 2-5

Comparative Example 2-5 was performed in the same manner as in Example 2-1 except that heating temperature was set to 50° C., and the oxygen-absorbing multilayered vials were measured for YI and the oxygen transmission rate. The results are shown in Table 2.

2014 (Japanese Patent Application No. 2014-021347), the contents of which are incorporated herein by reference.

INDUSTRIAL APPLICABILITY

The sterilized oxygen-absorbing resin composition, the sterilized oxygen-absorbing multilayer container, and the method for producing the same according to the present invention can be utilized as a material and the like of a container for storing various objects including foods, beverages, drugs, and cosmetics.

The invention claimed is:
1. A sterilized oxygen-absorbing resin composition obtained by performing at least:
   a sterilizing step of irradiating with radiation an oxygen-absorbing resin composition comprising a transition

TABLE 2

| | Type of radiation/ dose (kGy) | | Heating conditions | | YI of multilayered vial (values inside the parentheses[1] are ΔYI) | | | | |
|---|---|---|---|---|---|---|---|---|---|
| | | | | | | After radiation | | One week after | |
| | Gamma rays | Electron beams | Temperature/ °C. | Time/ min | Before radiation irradiation | irradiation/before heat treatment | After heat treatment | radiation irradiation | Oxygen transmission rate |
| Example 2-1 | 50 | — | 80 | 15 | −0.3 (0) | 31.6 (+31.9) | 14.9 (+15.2) | 12.3 (+12.6) | Under detection limit |
| Example 2-2 | 50 | — | 80 | 5 | −0.5 (0) | 31.7 (+32.2) | 25.3 (+25.8) | 22.3 (+22.8) | Under detection limit |
| Example 2-3 | 50 | — | 80 | 30 | −0.6 (0) | 31.4 (+32.0) | 9.3 (+9.9) | 6.5 (+7.1) | Under detection limit |
| Example 2-4 | 50 | — | 100 | 15 | −0.4 (0) | 31.7 (+32.1) | 9.3 (+9.7) | 6.5 (+6.9) | Under detection limit |
| Example 2-5 | 50 | — | 100 | 5 | −0.5 (0) | 31.4 (+31.9) | 21.6 (+22.1) | 19.0 (+19.5) | Under detection limit |
| Example 2-6 | 50 | — | 100 | 30 | −0.5 (0) | 31.7 (+32.2) | 8.9 (+9.4) | 6.3 (+6.8) | Under detection limit |
| Example 2-7 | 25 | — | 80 | 15 | −0.3 (0) | 19.9 (+20.2) | 9.9 (+10.2) | 7.8 (+8.1) | Under detection limit |
| Example 2-8 | 25 | — | 80 | 5 | −0.2 (0) | 19.7 (+19.9) | 13.6 (+13.8) | 10.7 (+10.9) | Under detection limit |
| Example 2-9 | 25 | — | 80 | 30 | −0.4 (0) | 20.1 (+20.5) | 7.2 (+7.6) | 5.8 (+6.2) | Under detection limit |
| Example 2-10 | 25 | — | 100 | 15 | −0.6 (0) | 19.7 (+20.3) | 7.3 (+7.9) | 5.9 (+6.5) | Under detection limit |
| Example 2-11 | 25 | — | 100 | 5 | −0.5 (0) | 19.6 (+20.1) | 10.5 (+11.0) | 8.3 (+8.8) | Under detection limit |
| Example 2-12 | 25 | — | 100 | 30 | −0.4 (0) | 19.7 (+20.1) | 7.0 (+7.4) | 5.7 (+6.1) | Under detection limit |
| Example 2-13 | — | 50 | 80 | 15 | −0.3 (0) | 30.3 (+30.6) | 12.7 (+13.0) | 9.8 (+10.1) | Under detection limit |
| Example 2-14 | — | 50 | 80 | 5 | −0.3 (0) | 30.5 (+30.8) | 23.1 (+23.4) | 20.4 (+20.7) | Under detection limit |
| Example 2-15 | — | 50 | 80 | 30 | −0.2 (0) | 30.3 (+30.5) | 8.4 (+8.6) | 6.1 (+6.3) | Under detection limit |
| Example 2-16 | — | 25 | 80 | 15 | −0.4 (0) | 17.7 (+18.1) | 8.0 (+8.4) | 6.2 (+6.6) | Under detection limit |
| Example 2-17 | — | 25 | 80 | 5 | −0.4 (0) | 18.0 (+18.4) | 11.8 (+12.2) | 9.2 (+9.6) | Under detection limit |
| Example 2-18 | — | 25 | 80 | 30 | −0.3 (0) | 17.7 (+18.0) | 7.0 (+7.3) | 5.6 (+5.9) | Under detection limit |
| Comparative Example 2-1 | 50 | — | — | — | −0.6 (0) | 31.6 (+32.2) | — | 27.2 (+27.8) | Under detection limit |
| Comparative Example 2-2 | 25 | — | — | — | −0.5 (0) | 19.9 (+20.4) | — | 17.2 (+17.7) | Under detection limit |
| Comparative Example 2-3 | — | 50 | — | — | −0.3 (0) | 30.4 (+30.7) | — | 25.1 (+25.4) | Under detection limit |
| Comparative Example 2-4 | — | 25 | — | — | −0.2 (0) | 18.1 (+18.3) | — | 15.9 (+16.1) | Under detection limit |
| Comparative Example 2-5 | 50 | — | 50 | 15 | −0.4 (0) | 31.5 (+31.9) | 28.8 (+29.2) | 26.7 (+27.1) | Under detection limit |

[1]Based on values before radiation irradiation

From the results of Examples described above, it was verified that, by performing heat treatment after radiation irradiation, the YI of multilayered vials more greatly decreased compared with those of Comparative Examples, and the low YI was maintained thereafter. Further, the oxygen-absorbing performance was maintained even after heat treatment. Thus, it was verified that the implementation of heat treatment had been very effective for fading the coloration due to radiation irradiation in a short time. Further, it was also verified that the vial of each Example showed no plastic deformation by heating and had good moldability.

The present application is based on Japanese Patent Application filed with the Japan Patent Office on Feb. 6, metal catalyst and a thermoplastic resin (a) having a tetralin ring as a constituent unit; and
a step of heating the oxygen-absorbing resin composition at a temperature equal to or higher than a glass transition temperature of the thermoplastic resin (a) and equal to or lower than 200° C., after the sterilizing step.

2. The sterilized oxygen-absorbing resin composition according to claim 1, wherein a time of the heating is 1 to 120 minutes.

3. The sterilized oxygen-absorbing resin composition according to claim 1, wherein the thermoplastic resin (a) is a polyester compound comprising a constituent unit having at least one tetralin ring selected from the group consisting of the following general formulas (1) to (4):

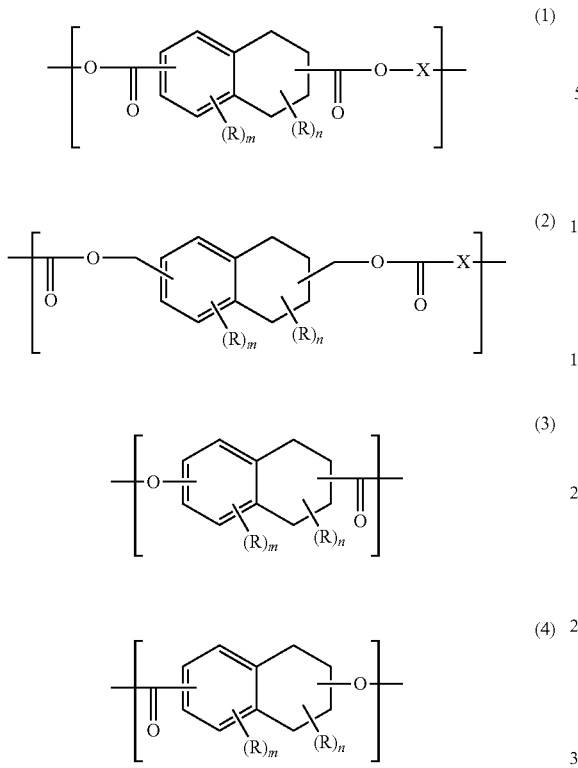

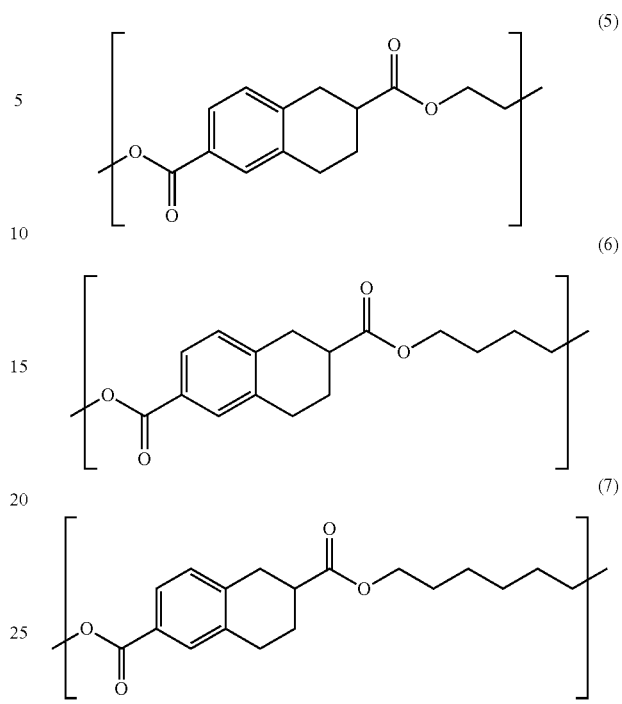

wherein R independently represents a hydrogen atom or a monovalent substituent; the monovalent substituent is at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, these of which may further have a substituent; m represents an integer of 0 to 3; n represents an integer of 0 to 7; at least one hydrogen atom is bonded to a benzylic position of the tetralin ring; and X represents a divalent group comprising at least one group selected from the group consisting of an aromatic hydrocarbon group, a saturated or unsaturated alicyclic hydrocarbon group, a linear or branched, saturated or unsaturated aliphatic hydrocarbon group, and a heterocyclic group.

4. The sterilized oxygen-absorbing resin composition according to claim 1, wherein the transition metal catalyst comprises at least one transition metal selected from the group consisting of manganese, iron, cobalt, nickel, and copper.

5. The sterilized oxygen-absorbing resin composition according to claim 1, wherein the transition metal catalyst is contained in an amount of 0.001 to 10 parts by mass in terms of the amount of a transition metal based on 100 parts by mass of the thermoplastic resin (a).

6. The sterilized oxygen-absorbing resin composition according to claim 1, wherein the constituent unit represented by the general formula (1) is at least one selected from the group consisting of the following formulas (5) to (7).

7. The sterilized oxygen-absorbing resin composition according to claim 1, wherein the radiation is at least one selected from the group consisting of gamma rays, X-rays, and electron beams.

8. A sterilized oxygen-absorbing multilayer container obtained by performing at least:
a sterilizing step of irradiating with radiation an oxygen-absorbing multilayer container comprising an oxygen-absorbing multilayer body, wherein the oxygen-absorbing multilayer body comprises at least an oxygen absorbing layer (layer A) comprising an oxygen-absorbing resin composition comprising a transition metal catalyst and a thermoplastic resin (a) having a tetralin ring as a constituent unit and a layer (layer B) comprising a thermoplastic resin (b) formed on the oxygen absorbing layer (layer A); and
a step of heating the oxygen-absorbing multilayer container at a temperature equal to or higher than a glass transition temperature of the thermoplastic resin (a) and equal to or lower than 200° C., after the sterilizing step.

9. The sterilized oxygen-absorbing multilayer container according to claim 8, wherein:
the oxygen-absorbing multilayer container comprises an oxygen-absorbing multilayer body having three or more layers, the oxygen-absorbing multilayer body comprising at least
the oxygen absorbing layer (layer A),
a layer (layer B1) comprising a thermoplastic resin (b1) formed on one surface of the oxygen absorbing layer (layer A), and
a layer (layer B2) comprising a thermoplastic resin (b2) formed on an other surface of the oxygen absorbing layer (layer A); and
the temperature of the heating step is equal to or higher than the glass transition temperature of the thermoplastic resin (a) and equal to or lower than either a glass transition temperature of the thermoplastic resin (b1) or a glass transition temperature of the thermoplastic resin (b2).

10. A method for producing a sterilized oxygen-absorbing multilayer container, comprising:

a sterilizing step of irradiating with radiation an oxygen-absorbing multilayer container comprising an oxygen-absorbing multilayer body, wherein the oxygen-absorbing multilayer body comprises at least an oxygen absorbing layer (layer A) comprising an oxygen-absorbing resin composition comprising a transition metal catalyst and a thermoplastic resin (a) having a tetralin ring as a constituent unit and a layer (layer B) comprising a thermoplastic resin (b) formed on the oxygen absorbing layer (layer A); and a step of heating the oxygen-absorbing multilayer container at a temperature equal to or higher than a glass transition temperature of the thermoplastic resin (a) and equal to or lower than 200° C., after the sterilizing step.

* * * * *